United States Patent [19]
Filipi et al.

[11] Patent Number: 5,226,876
[45] Date of Patent: Jul. 13, 1993

[54] OPERATING CHANNEL/INSUFFLATION PORT ASSEMBLIES

[75] Inventors: Charles J. Filipi, Marshalltown, Iowa; Thomas R. DeMeester, San Marino, Calif.; Rebecca C. Gibbs, Burlington, N.C.; Ronald A. Hinder, Omaha, Nebr.

[73] Assignee: Wilson Cook Medical, Inc., Winston-Salem, N.C.

[21] Appl. No.: 837,862

[22] Filed: Feb. 18, 1992

Related U.S. Application Data

[63] Continuation-in-part of Ser. No. 608,339, Nov. 2, 1990, Pat. No. 5,088,979, which is a continuation-in-part of Ser. No. 595,977, Oct. 11, 1990, abandoned.

[51] Int. Cl.$^5$ .......................................... A61M 37/00
[52] U.S. Cl. ..................................... 604/26; 604/174
[58] Field of Search ....................... 604/26, 174; 128/4

[56] References Cited

U.S. PATENT DOCUMENTS

| | | | |
|---|---|---|---|
| 3,817,251 | 6/1974 | Hasson | 604/26 |
| 4,077,412 | 3/1978 | Mooson | 604/174 X |
| 4,207,872 | 6/1980 | Meiri et al. | 128/4 |
| 4,240,411 | 12/1988 | Hosono | 128/4 |
| 5,002,557 | 3/1991 | Hasson | 604/26 X |

*Primary Examiner*—William H. Grieb
*Attorney, Agent, or Firm*—Woodard, Emhardt, Naughton, Moriarty & McNett

[57] ABSTRACT

Operating channel/insufflation port assemblies are disclosed herein which facilitate the operation of percutaneous surgical procedures with remotely operable instrumentation. In one of the disclosed assemblies, an operating channel/insufflation port member defines an operating channel sized to receive remotely operable instrumentation, and an insufflation lumen. The port assembly is anchorable in place, extending percutaneously into the stomach with remotely operable instrumentation being advanceable through the operating channel and into the stomach, and with $CO_2$ being passable into the stomach through the insufflation lumen. An insufflation valve member, connectable to said insufflation port, provides means for variably controlling the supply of $CO_2$ into the stomach while a sealing member prevents gas leakage through the operating channel during operation/insufflation by providing a seal between the port member and the remotely operable instrumentation received therethrough.

In a second disclosed assembly, the operating channel/insufflation port member defines an operating channel sized to receive remotely operable instrumentation, and a dual purpose inflation/insufflation lumen. The port assembly is anchorable in place by a balloon which is inflatable through the inflation/insufflation lumen. After the balloon has been inflated, an inflation/insufflation tube within the inflation/insufflation lumen is advanced to seal the inflated balloon and open an insufflation port, through which a positive pressure may be maintain within the stomach during a subsequent surgical procedure performed through the operating channel. Also provided are a set of seals which prevent gas leakage both during and after operation/insufflation.

7 Claims, 8 Drawing Sheets

OPERATING CHANNEL/INSUFFLATION PORT ASSEMBLIES

REFERENCE TO RELATED APPLICATIONS AND PATENT

This application is a continuation-in-part of co-pending U.S. patent application, Ser. No. 608,339, filed on Nov. 2, 1990 U.S. Pat. No. 5,088,979 and entitled Method for Esophageal Invagination and Devices useful therefor which application is a continuation-in-part of a prior U.S. patent application, Ser. No. 595,977, filed Oct. 11, 1990 and entitled Method and Device for Esophageal Invagination, now abandoned. The above referenced U.S. patent application, Ser. No. 608,339, has been allowed and U.S. Pat. No. 5,088,979 is being issued thereon on the date of the filing of this application, Feb. 18, 1992.

BACKGROUND OF THE INVENTION AND INCORPORATION BY REFERENCE

The present invention relates to operating channel/insufflation port assemblies which are useful in a technique for minimally-invasive invagination of the esophagus at the gastroesophageal junction described in the above referenced co-pending patent application, Ser. No. 608,339, the complete disclosure of which is hereby incorporated by reference. The operating channel/insufflation port assemblies described and claimed herein are useful for other minimally-invasive techniques as well in which an operation is performed percutaneously with remotely operable instrumentation through an operating port while a positive internal pressure is maintained during the operation.

SUMMARY OF THE INVENTION

Generally speaking, the present invention provides new and improved devices which are useful in a technique for minimally-invasive invagination of the esophagus at the gastroesophageal junction. The present invention specifically provides operating channel/insufflation port assemblies which are useful for performing the above mentioned technique, as well as other minimally-invasive techniques where an operation is to be performed percutaneously with remotely operable instrumentation through an operating port and a positive internal pressure is to be maintained during the operation.

According to one embodiment, an operating channel/insufflation port assembly includes an operating channel/insufflation port member which defines an operating channel sized to receive remotely operable instrumentation, and an insufflation lumen. The port assembly is anchorable in place, extending percutaneously into the stomach with remotely operable instrumentation being advanceable through the operating channel and into the stomach, and with $CO_2$ being passable into the stomach through said insufflation lumen. An insufficient valve member, connectable to said insufflation port, provides means for variably controlling the supply of $CO_2$ into the stomach while a sealing member prevents gas leakage through the operating channel during operation/insufflation by providing a seal between the port member and the remotely operable instrumentation received therethrough.

In a second disclosed embodiment, an operating channel/insufflation port member defines an operating channel sized to receive remotely operable instrumentation, and a dual purpose inflation/insufflation lumen. The port assembly is anchorable in place by a balloon which is inflatable through the inflation/insufflation lumen. After the balloon has been inflated, an inflation/insufflation tube within the inflation/insufflation lumen is advanced to seal the inflated balloon and open an insufflation port, through which a positive pressure may be maintain within the stomach during a subsequent surgical procedure performed through the operating channel. Also provided are a set of seals which prevent gas leakage both during and after operation/insufflation.

BRIEF DESCRIPTION OF THE DRAWINGS

FIG. 1a is a side elevational view of a complete assembly. FIGS. 1b-d illustrate enlarged cross-sectional views of portions of the assembly at various stages of operation. FIG. 1b shows an implanted operating channel/insufflation port 110, balloon inflation nozzle 130, and insufflation valve 140, with nozzle 130 and valve 140 detached from their respective connection ports. In FIG. 1c, tapered portion 111 of port 110 has been severed, and remotely operable instrument 50 has been inserted through central operating channel 114. Also in FIG. 1c, insufflation valve 140 has been attached to insufflation port 115 for insufflation of the stomach through insufflation lumen 116, and sealing member 150 has been placed about port 110 and positioned in sealing engagement with remotely operable instrument 50, thus preventing gas leakage through operating channel 114 during the operation/insufflation. In FIG. 1d, remotely operable instrument 50 has been removed, insufflation valve 140 has been detached, and seal cap 160 has been placed about port 110, sealing access to and from the stomach.

FIG. 2a shows cross-sectioned portions of an operating channel/insufflation port 210 with balloon 218 in a deflated state. In FIG. 2b, tapered portion 211 of port 110 has been removed, and sealing member 250 and inflation/insufflation member 298 have been placed into their respective positions for sealing of the operating channel 214 and for inflation of balloon 218. Also in FIG. 2b insufflation valve 240 has been attached to inflation/insufflation member 298 for inflation of balloon 218. In FIG. 2c, remotely operable instrument 50 has been placed in position for remote percutaneous operation, and inflation/insufflation member 298 has been advanced into position for insufflation of the stomach. In FIG. 1d, remotely operable instrument 50 has been removed, insufflation valve 240 has been detached, and seal plugs 260 and 270 have been placed into operating channel 214 and connector 298a respectively, sealing access to and from the stomach.

DESCRIPTION OF THE PREFERRED EMBODIMENT

Figure 1A:
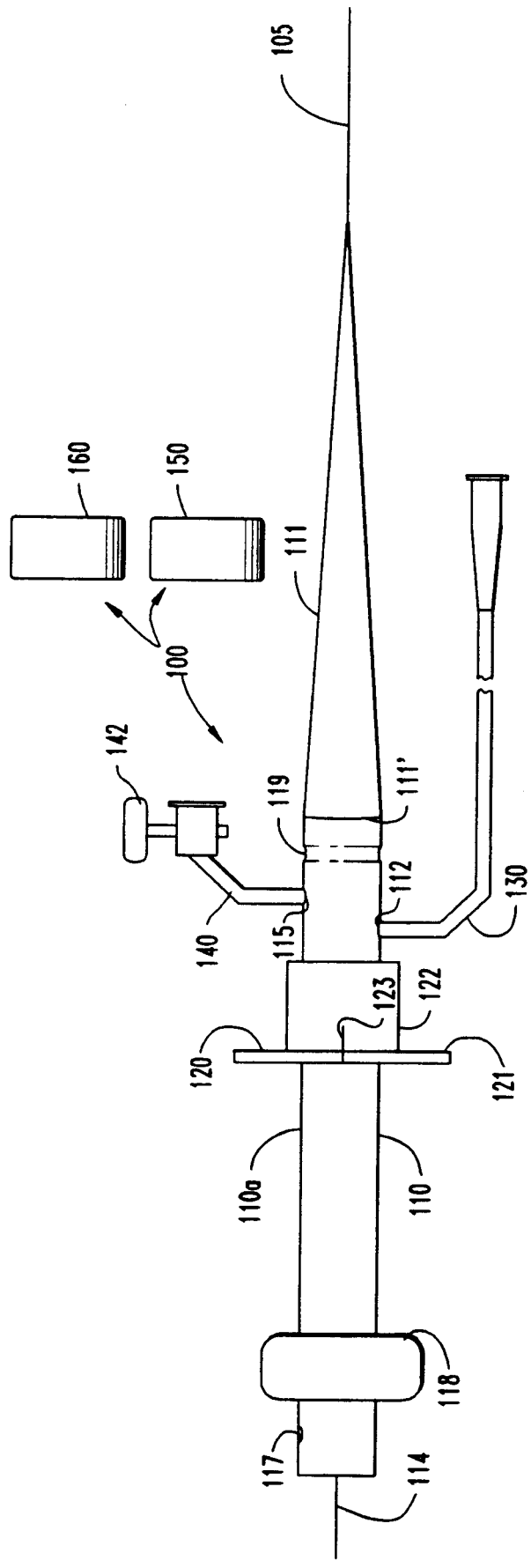
FIGS. 1a-d illustrate an operating channel/insufflation assembly which provides percutaneous access into the stomach for introduction of a remotely operable instrument, and also provides for the insufflation of the stomach.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

An operating channel/insufflation port assembly useful for the introduction of a remotely operable instrument 50 will now be discussed in specific detail in relation to FIGS. 1a–d. Operating channel/insufflation port assembly 100 includes guide wire 105, operating channel/insufflation port 110, skin flange 120, attachable balloon inflator nozzle 130, attachable insufflation valve 140, sealing member 150, and seal cap 160.

An operating channel/insufflation port may be percutaneously opened into the stomach by 1) percutaneously introducing a guide wire into the stomach, 2) using an endoscopic to snare the guide wire and retract it through the mouth, 3) advancing a graduated dilator operating channel port assembly transorally over the guide wire under tension and partially out through the skin, and 4) anchoring the assembly into place. Specifically, guide wire 105 is first percutaneously introduced into the stomach, and an endoscope is introduced transorally into the stomach and used to snare guide wire 105 and retract it through the mouth. Operating channel/insufflation port 110 is then transorally advanced over guide wire 105 under tension and partially out through the skin. After removing guide wire 105, skin flange 120 is placed over the tubular portion of port 110 and advanced toward the skin. Attachable balloon inflator nozzle 130 is then attached to inflation port 112 and $CO_2$ is injected therethrough and into balloon 118, through inflation lumen 113 which is connected thereto, thus inflating balloon 118 in place with the stomach. Skin flange 120 is then adjusted against the skin to secure port 110 into place. The tapered distal portion 111 of operating channel/insufflation port 110 is then cut off at mark 111', thereby opening access into the stomach through operating channel 114.

When connected to insufflation port 115, insufflation valve 140 is operated to provide a supply of $CO_2$ into the stomach through insufflation lumen 116 and out insufflation opening 117. By turning cock 142, the supply of $CO_2$ into the stomach may be variably controlled and adjusted as needed.

Operating channel/insufflation port 110 is preferably made of flexible material which matches the elasticity of the tissue surrounding it when implanted. Silicone is believed to be particularly suited for this purpose. To provide additional strength and stability during implantation, tapered portion 111 of port 110 has a lumen 104 of only enough size to receive wire guide 105. As previously discussed, tapered portion 111 is severed after implantation to expose central operating channel 114, thereby providing access into the stomach for remotely operable instrumentation which is to be used in conjunction with the operation to be performed.

Skin flange 120 is also made of silicone, and includes of a disc shaped flange 121 and a tubular handle portion 122. Slot 123 facilitates the advancing of flange 120 along port 110. Seal cap 150 seals the end of port 110, attaching thereabout to form a sealing fit between detent 151 of seal cap 150 and indentation 119 of port 110.

Figure 1B:
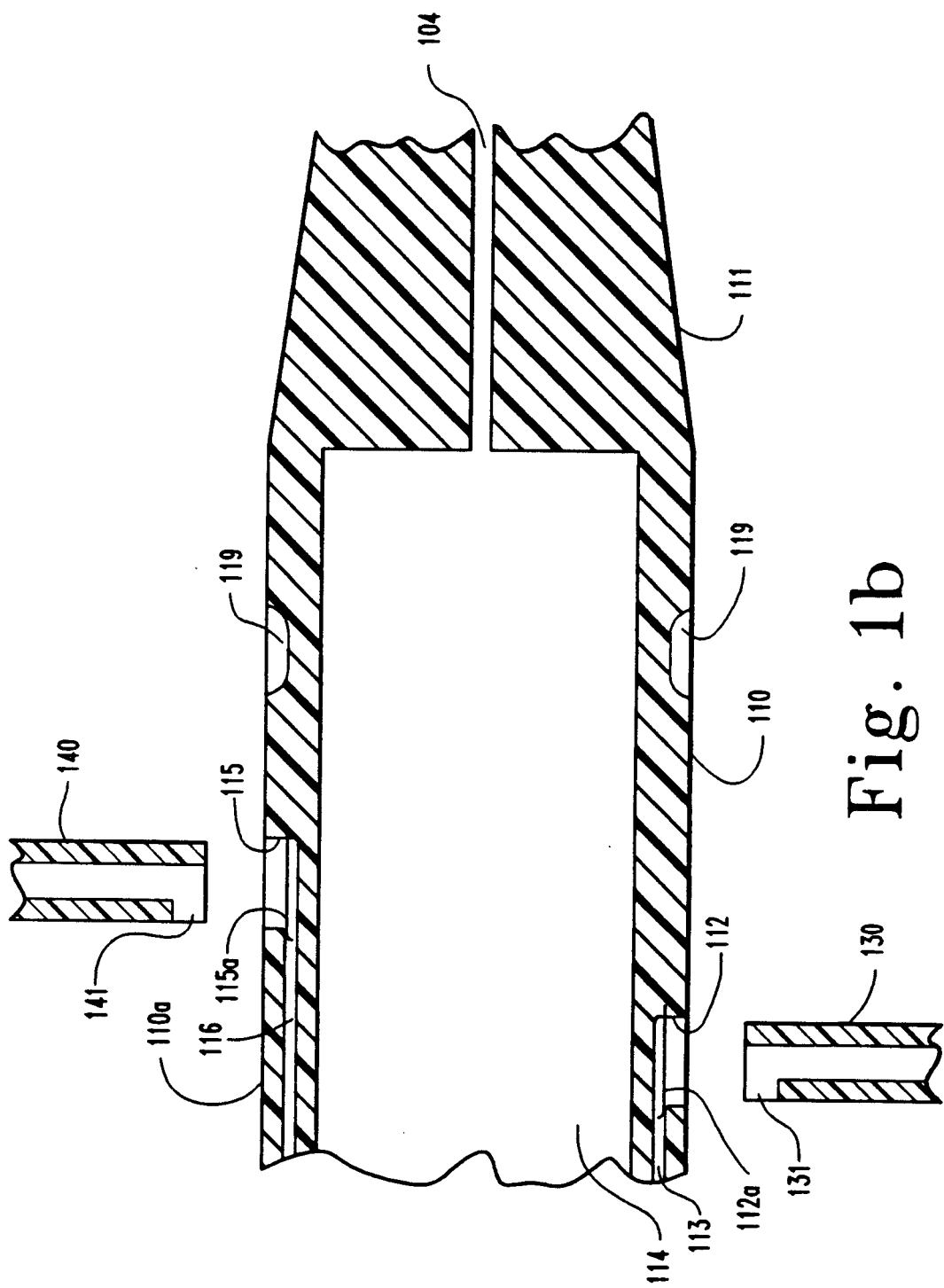
Figure 1C:
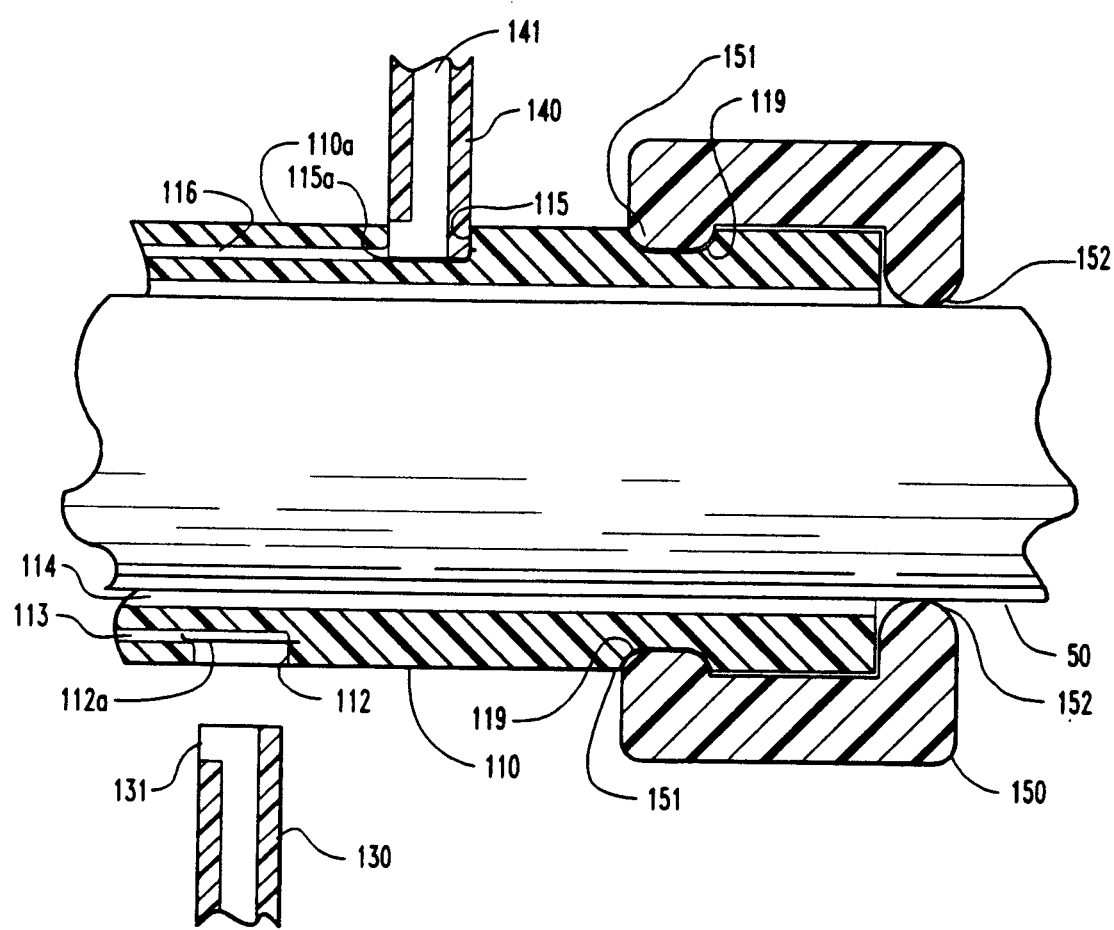
Figure 1D:
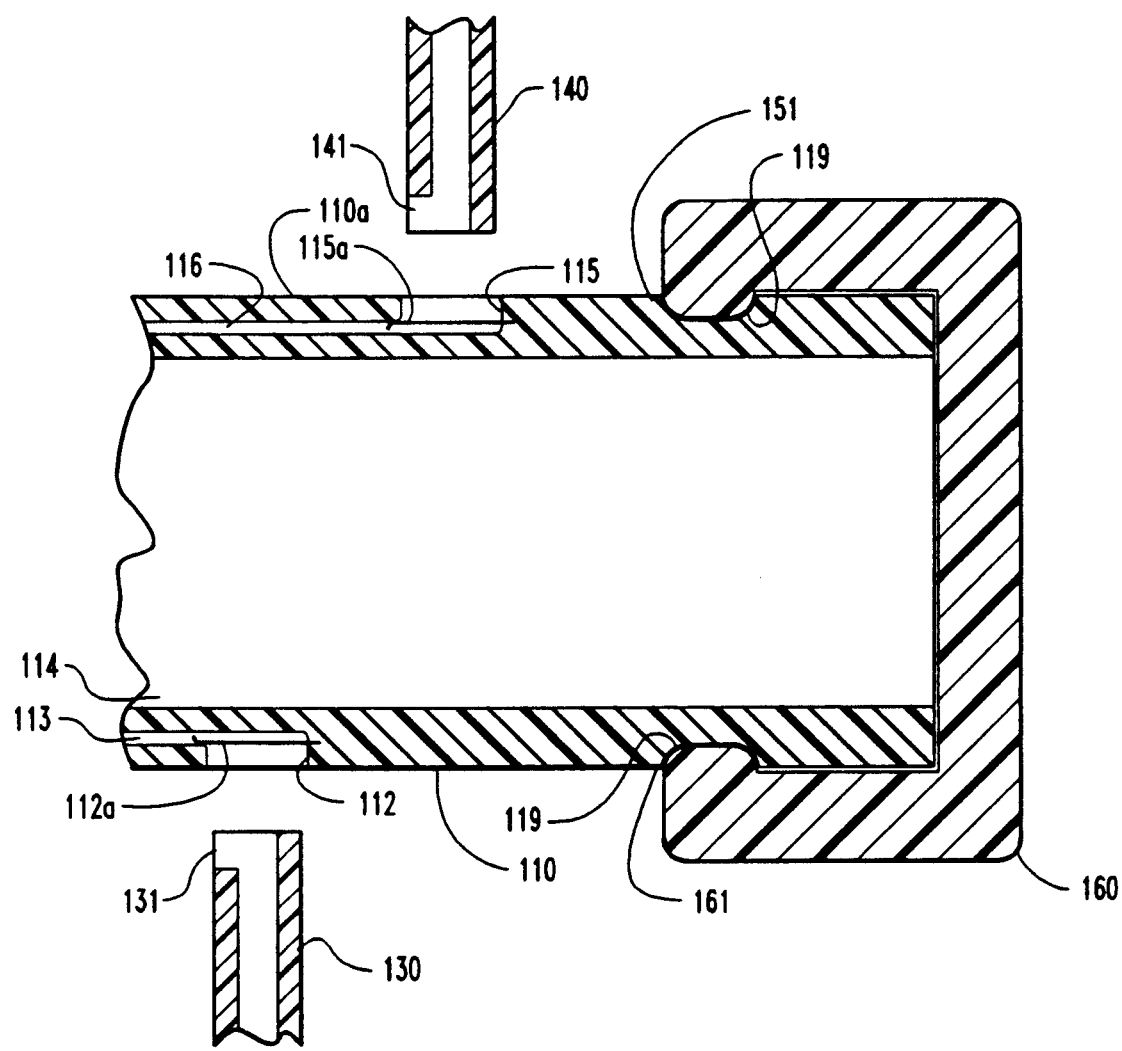

FIGS. 1b–d illustrate enlarged cross-sectional views of portions of the assembly at various stages of operation. FIG. 1b shows an implanted operating channel/insufflation port 110, balloon inflation nozzle 130, and insufflation valve 140, with nozzle 130 and valve 140 detached from their respective connection ports. In FIG. 1b it can been seen that tapered portion 111 has a central lumen 104 sized only to receive guide wire 105, thus providing additional strength and stability during implantation, while tubular portion 110a defines an enlarged operating channel 114, sized to receive remotely operable instrumentation (12 mm, for example, for a fastening assembly, and 7 mm, for a laparoscope). Within the walls of said tubular portion 110a are defined a balloon inflation port 112 and balloon inflation lumen 113 which connects port 112 to the interior of balloon 118. At the entrance of port 112 is seal 112a. Also defined within the walls of tubular portion 110a is an insufflation lumen 116, connecting exterior insufflation port 115 to interior insufflation port 117. At the entrance of port 115 is seal 115a.

Also shown in FIGS. 1b–d are partial cross-sectional views of balloon inflation nozzle 130 and insufflation valve 140, which are connectable to ports 112 and 115 respectively. When placed into port 115, as shown in FIG. 1c, seal 115a is opened, allowing $CO_2$ to be injected into the stomach through valve passageway 141 and insufflation lumen 116. When valve 140 has been removed from port 115, as shown in FIG. 1d, seal 115a recloses. Balloon inflation nozzle 130 operates in the same manner in relation to port 112 to inflate balloon 118 through passageway 131 and inflation lumen 113.

In FIG. 1c, tapered portion 111 of port 110 has been severed, and remotely operable instrument 50 has been inserted through central operating channel 114. Also in FIG. 1c, insufflation valve 140 has been attached to insufflation port 115 for insufflation of the stomach through insufflation lumen 116. Sealing member 150 has been placed about port 110 and positioned in sealing engagement with remotely operable instrument 50, the preventing gas leakage through operating channel 114 during operation/insufflation. Detent 151 of sealing member 150 fits indentation 119 of port 110 in sealing engagement, while interior flange 152 forms a sealing engagement with remotely operable instrument 50 to effectively prevent leakage.

In FIG. 1d, remotely operable instrument 50 has been removed, insufflation valve 140 has been detached, and seal cap 160 has been placed about port 110, sealing access to and from the stomach. So sealed, port 110 may be kept implanted for a period of time after completion of the above described operation in order to maintain fixation of the stomach to the peritoneum and also provides a drainage port for the stomach.

A second operating channel/insufflation port assembly will now be discussed with reference to FIGS. 2a–d. FIGS. 2a–d illustrate enlarged cross-sectional views of portions of operating channel/insufflation assembly 200 at various stages of operation. It is to be noted that FIGS. 2a–d and the following discussion thereof are addressed to the differences in structure and function between assemblies 100 and 200. Where not indicated, relative corresponding portions of assemblies 100 and 200 are considered to have the same construction and purpose. With this understanding, corresponding reference numerals in the 100 and 200 series have been assigned for the same corresponding elements of assemblies 100 and 200.

Figure 2A:
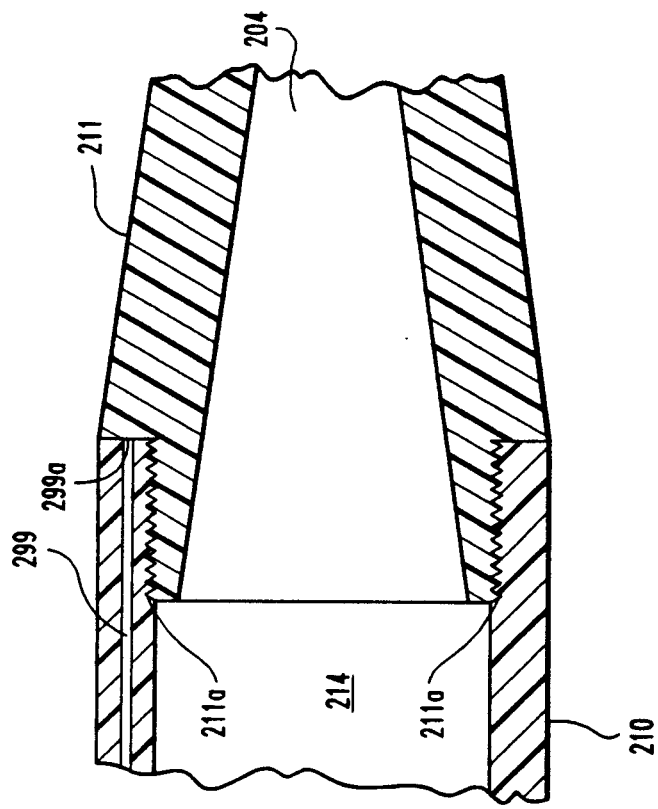
FIGS. 2a-d illustrate enlarged cross-sectional views of portions of a second operating channel/insufflation assembly at various stages of operation.
Figure 2A:
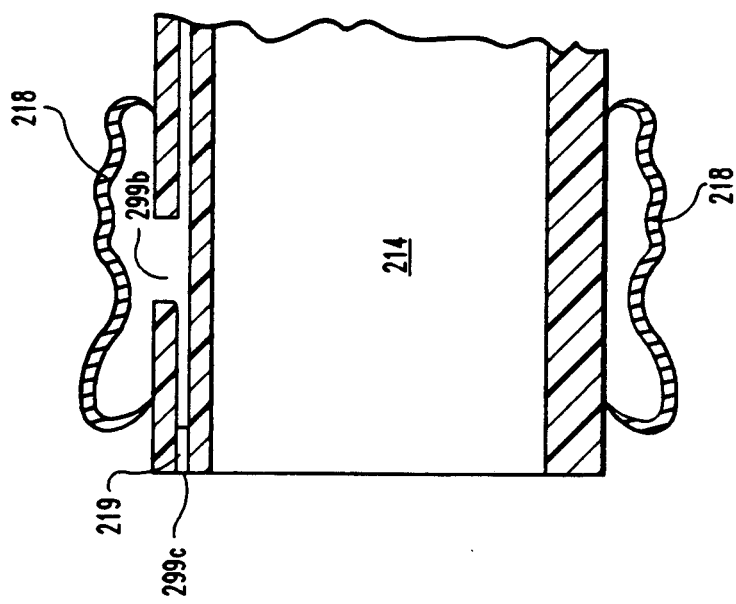

FIGS. 2a shows cross-sectioned portions of an operating channel/insufflation port 210 with balloon 218 in a deflated state. In FIG. 2a, it is seen that dilator 211 is threadably engaged to port 210 by cooperative threading 211a, thereby allowing for the removal of dilator to expose operating channel 214 after implantation by simply unscrewing dilator 211 form port 210. Dilator 211 also defines a frustoconically shaped lumen 204 there in for receiving a guide wire therethrough. FIG. 2a also shows a single dual purpose inflation/insufflation lumen 299 within port 210, which defines an entrance port 299a, an inflation exit port 299b, and an insufflation exit port 299c, all in fluid communication therebetween, and which thereby provides a conduit both for the inflation of balloon 218 and the insufflation of the stomach. By the utilization of dual purpose inflation/insufflation lumen 299 in lieu of separate lumens as described in relation to assembly 100, the overall diameter of port 210 can be reduced relative to the size of the instrumentation to be used through port 210, thereby providing for a smaller diameter implantation and thus a less invasive overall procedure. The manner in which inflation/insufflation lumen 299 is utilized to provide for both inflation and insufflation will be discussed in relation to FIGS. 2b–c.

Figure 2B:
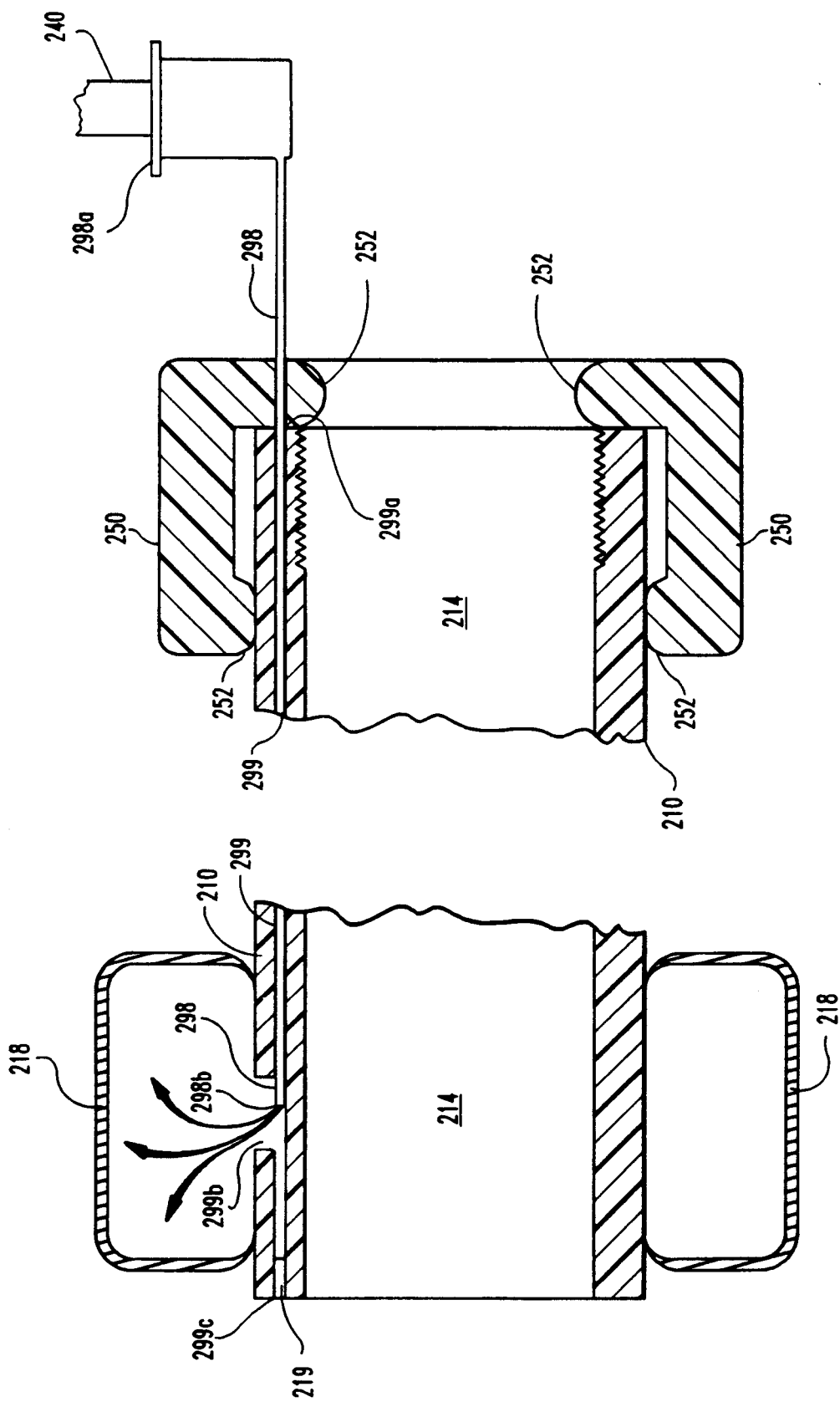

In FIG. 2b, dilator 211 has been removed from port 210, and sealing member 250 and inflation/insufflation tube 298 have been placed into their respective positions for sealing of the operating channel 214 and for inflation of balloon 218. As is seen in FIG. 2b, sealing member 250 defines a passageway 258 for receiving inflation/insufflation tube 298 therethrough and into entrance port 299a of inflation/insufflation lumen 299. Also in FIG. 2b, insufflation valve 240 has been attached to connector 298a for inflation/insufflation tube 298, and balloon 218 is shown being inflated by the supplying of gas out the end portion 298b of tube 298 and through inflation port 299b. In this configuration, plug 219 seals insufflation exit port 299c of lumen 299, thereby preventing insufflation and allowing for inflation of balloon 218 to occur.

Figure 2C:
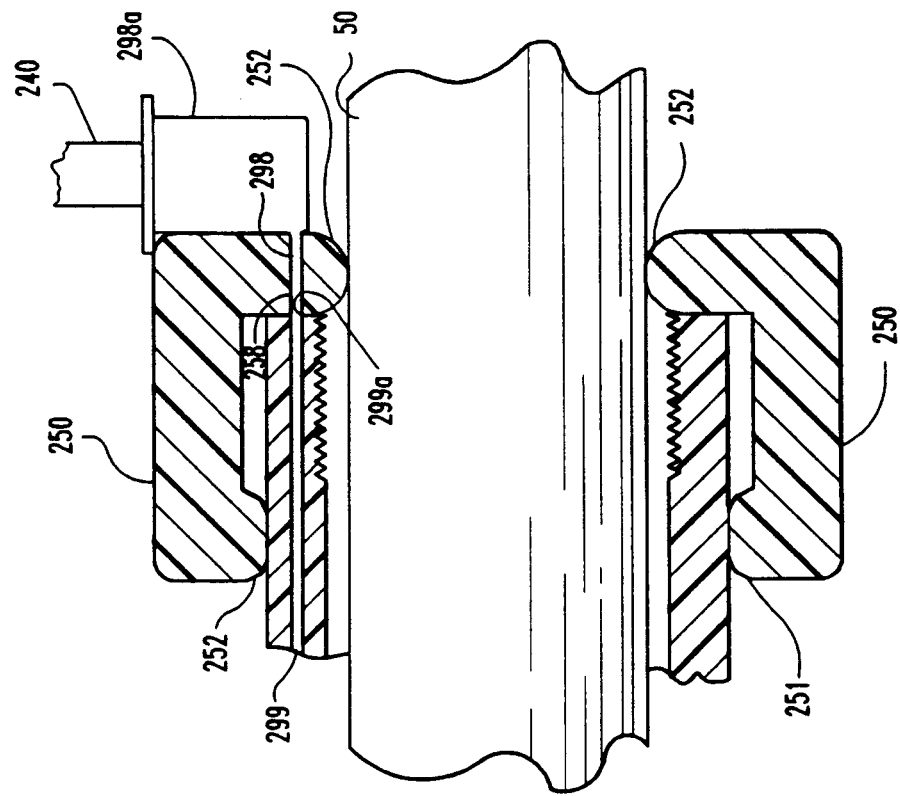
Figure 2C:
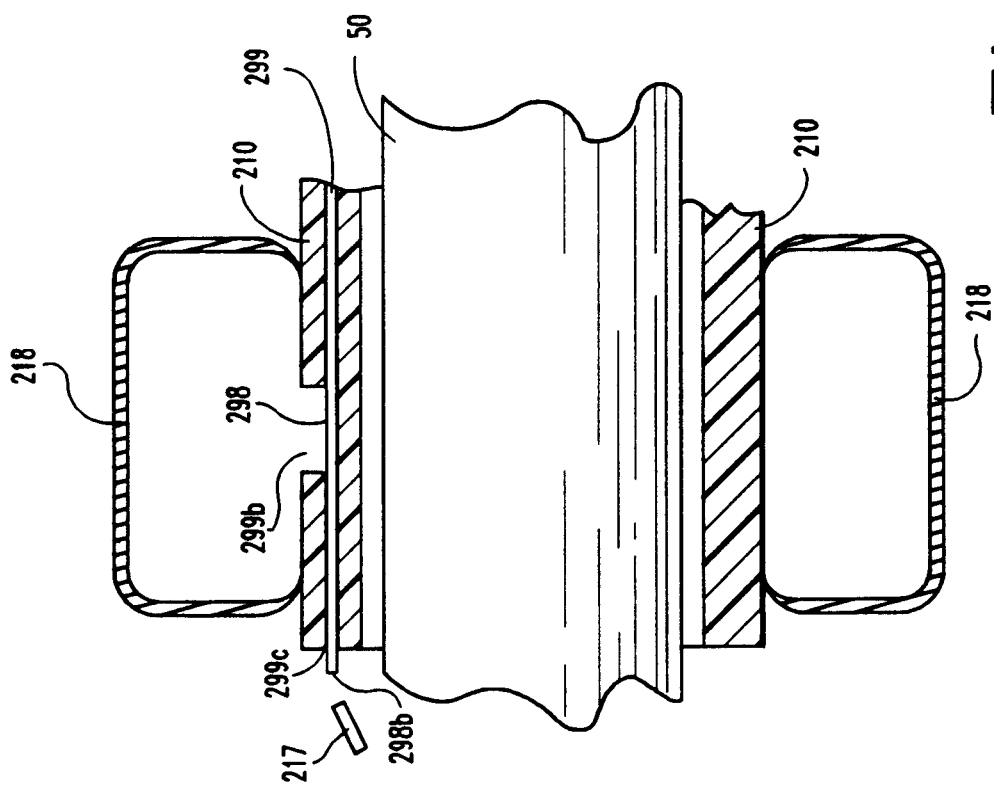
Figure 2D:
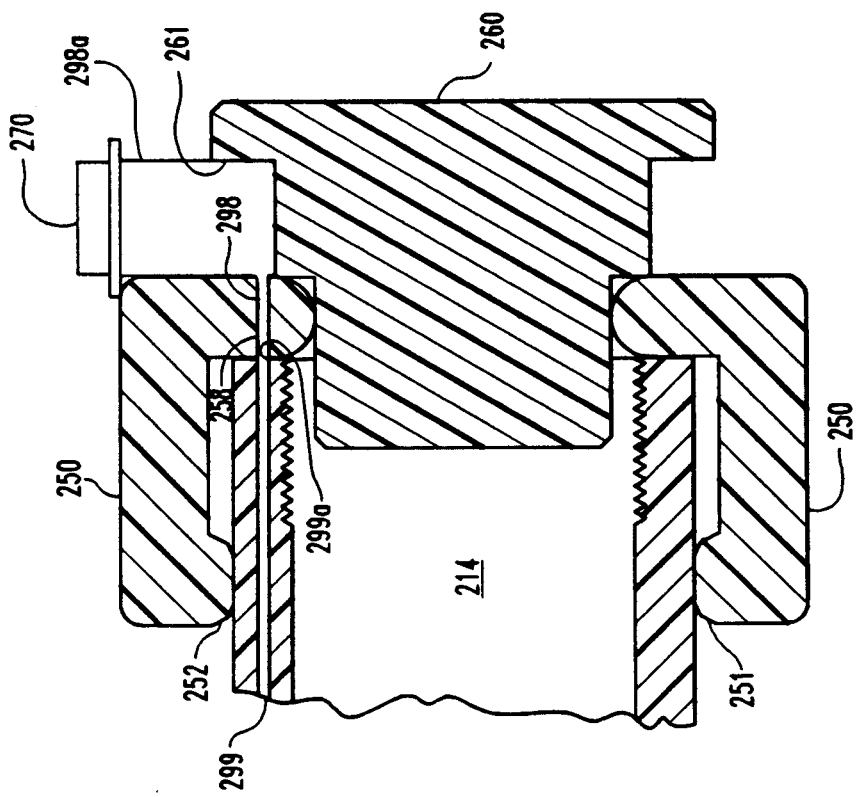
Figure 2D:
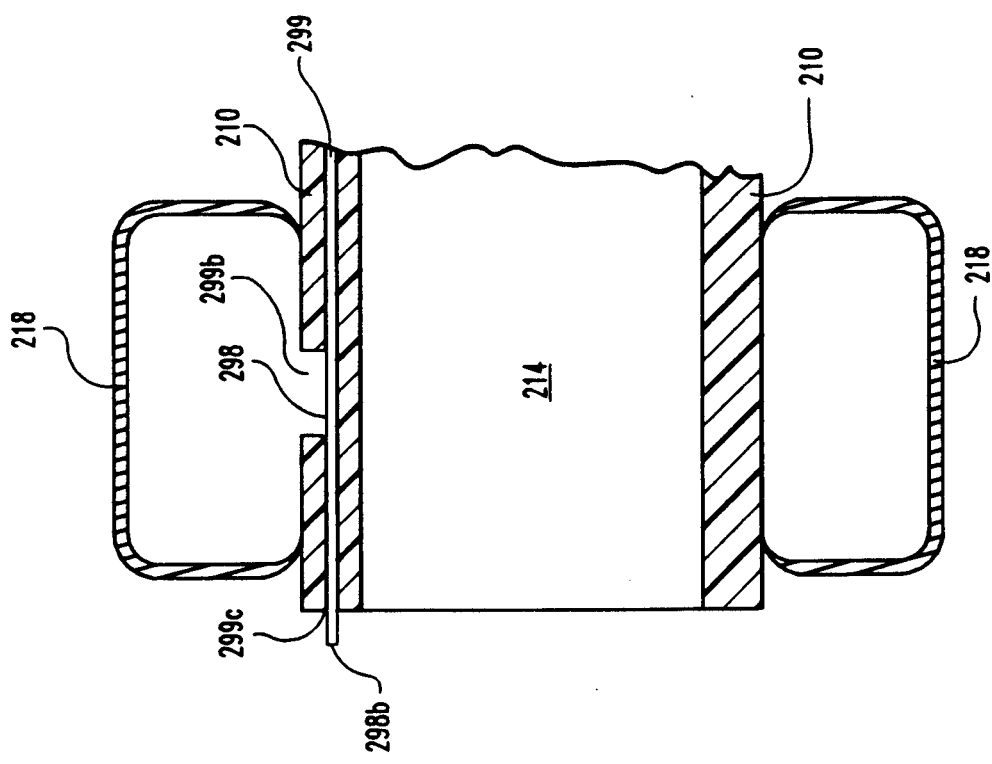

In FIG. 2c, remotely operable instrument 50 has been placed in position for remote percutaneous operation, and inflation/insufflation tube 298 has been advanced into position for insufflation of the stomach. By so advancing tube 298, and portion 298b of tube 298 pushes plug 219 out of insufflation exit port 299c, thereby allowing for insufflation of the stomach through tube 298. At the same time, the advancing of tube 298 closes inflation port 299b, thereby sealing port 299b to cause balloon 218 to be maintained in an inflated state.

In FIG. 1d, remotely operable instrument 50 has been removed, insufflation valve 240 has been detached, and seal plugs 260 and 270 have been placed into operating channel 214 and connector 298a respectively, sealing access to and from the stomach. In this configuration, shoulder portion 261 of seal plug 260 also acts to maintain connector against sealing member 250, thereby maintaining inflation/insufflation tube 298 in position to seal portion 299b and keep balloon 218 in its inflated state.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. An operating channel/insufflation port assembly comprising:
   an operating channel/insufflation port member, said operating channel/insufflation port member defining an operating channel sized to receive remotely operable instrumentation, said port member further defining an insufflation lumen connecting to an insufflation port located on the exterior of said port member;
   anchoring means for anchoring said port member in place extending percutaneously into the stomach, with remotely operable instrumentation being advanceable through said operating channel and into the stomach, and with gas being passable into the stomach through said insufflation lumen;
   an insufflation valve member, connectable to said insufflation port, said insufflation valve member including means for variably controlling the supply of gas into the stomach through said insufflation lumen;
   operating channel sealing means for preventing gas leakage during operation/insufflation, said sealing means including means for providing a seal between said operating channel/insufflation port member and remotely operable instrumentation received therethrough; and
   postoperative sealing means for sealing said operating channel and said insufflation lumen upon removal of said remotely operable instrumentation and said insufflation valve member respectively.

2. The operating channel/insufflation port assembly of claim 1 in which said anchoring means includes an inflatable balloon, and said port member further defines an inflation lumen an inflation entrance port and an inflation exit port in communication therewith, the interior of said inflatable balloon being in fluid communication with said inflation exit port of said inflation lumen.

3. An operating channel/insufflation port assembly comprising:
   an operating channel/insufflation port member, said operating channel/insufflation port member defining an operating channel sized to receive remotely operable instrumentation, said port member further defining a single inflation/insufflation lumen, said inflation/insufflation lumen having, in fluid communication, an entrance port, an inflation exit port, and an insufflation exit port;
   anchoring means for anchoring said port member in place extending percutaneously into the stomach, with remotely operable instrumentation being advanceable through said operating channel and into the stomach, and with said insufflation exit port positioned within the stomach, said anchoring means including an inflatable balloon, the interior of said inflatable balloon being in fluid communication with said inflation exit port of said inflation/insufflation lumen;
   an inflation/insufflation tube positionable within said inflation/insufflation lumen, said tube being positionable in a first inflation position in which said inflation/insufflation tube exits in fluid communication with said inflation exit port of said inflation/insufflation lumen, and a second insufflation position in which said inflation/insufflation tube exits in fluid communication with said insufflation exit port of said inflation/insufflation lumen;
   an inflation/insufflation valve member, connectable to said inflation/insufflation tube, said valve member including means for variably controlling the supply of gas into said balloon and into the stomach through said inflation/insufflation tube; and operating channel sealing means for preventing gas leakage during operation/insufflation, said sealing means including means for providing a seal between said operating channel/insufflation port member and remotely operable instrumentation received therethrough.

4. The operating channel/insufflation port assembly of claim 3 additionally comprising means for closing said insufflation exit port during the inflation of said balloon through said inflation exit port; means for opening said insufflation exit port after the inflation of said balloon has occurred; and means for closing said inflation exit port after the inflation of said balloon and during the insufflation of the stomach through said insufflation exit port.

5. The operating channel/insufflation port assembly of claim 4 in which said means for closing said insufflation exit port during the inflation of said balloon through said inflation exit port includes a plug positioned within said inflation/insufflation lumen at said insufflation exit port;

said means for opening said insufflation exit port after the inflation of said balloon has occurred includes said tube being advanceable to push said plug out of said inflation/insufflation lumen; and said means for closing said inflation exit port after the inflation of said balloon and during the insufflation of the stomach through said insufflation exit port includes said inflation exit port being sealed by said tube when said tube is advanced into said insufflation position.

6. The operating channel/insufflation port assembly of claim 3 additional comprising postoperative sealing means for sealing said operating channel and said inflation/insufflation lumen upon removal of said remotely operable instrumentation and said inflation/insufflation valve member respectively.

7. The operating channel/insufflation port assembly of claim 5 additional comprising postoperative sealing means for sealing said operating channel and said inflation/insufflation lumen upon removal of said remotely operable instrumentation and said inflation/insufflation valve member respectively.

* * * * *

UNITED STATES PATENT AND TRADEMARK OFFICE
CERTIFICATE OF CORRECTION

PATENT NO. : 5,226,876

DATED : July 13, 1993

INVENTOR(S) : Dr. Charles Joesph Filipi et al.

It is certified that error appears in the above-identified patent and that said Letters Patent is hereby corrected as shown below:

On the title page, in the Abstract, line 30, please change "maintain" to --maintained--.

In column 1, line 58, please change "insufficient" to --insufflation--.

In column 2, line 8, please change "maintain" to --maintained--.

In column 3, line 19, please change "endoscopic" to --endoscope--.

In column 3, line 36, please change "with" to --within--.

In column 3, line 61, please delete "of".

In column 4, line 37, please change "the" to --thus--.

In column 4, line 66, please change "FIGS." to --FIG.--.

In column 5, line 4, please change "form" to --from--.

In column 5, line 6, please change "there in" to --therein--.

In column 5, line 44, please change "and" to --end--.

In column 5, line 58, please change "portion" to --port--.

In column 6, line 34, after "lumen" please insert --having--.

In column 8, line 14, please change "additional" to --additionally--.

UNITED STATES PATENT AND TRADEMARK OFFICE
CERTIFICATE OF CORRECTION

PATENT NO. : 5,226,876
DATED : July 13, 1993
INVENTOR(S) : Dr. Charles Joesph Filipi, et. al.

It is certified that error appears in the above-indentified patent and that said Letters Patent is hereby corrected as shown below:

In column 8, line 20, please change "additional" to --additionally--.

Signed and Sealed this

Twenty-fourth Day of October, 1995

Attest:

BRUCE LEHMAN

Attesting Officer

Commissioner of Patents and Trademarks